United States Patent [19]

DeSimone et al.

[11] Patent Number: 4,812,536
[45] Date of Patent: Mar. 14, 1989

[54] SELECTIVE PARA-ETHYLATION OF TOLUENE WITH MAGNESIUM COMPOUND-IMPREGNATED, CRYSTALLINE, GALLOSILICATE BASED, MOLECULAR SIEVE CATALYST COMPOSITIONS

[75] Inventors: Richard E. DeSimone, Lisle; Lori B. Lane, Wheaton, both of Ill.

[73] Assignee: Amoco Corporation, Chicago, Ill.

[21] Appl. No.: 202,210

[22] Filed: Jun. 3, 1988

Related U.S. Application Data

[63] Continuation of Ser. No. 901,613, Aug. 29, 1986, abandoned.

[51] Int. Cl.$^4$ ................................................. C07C 2/68
[52] U.S. Cl. .................................................... 585/467
[58] Field of Search ......................................... 585/467

[56] References Cited

U.S. PATENT DOCUMENTS 3,702,886 11/1972 Argauer et al. ..................... 423/328
4,086,287 4/1978 Kaeding et al. .................... 585/467

FOREIGN PATENT DOCUMENTS 60-19726 1/1985 Japan.

Primary Examiner—Curtis R. Davis
Attorney, Agent, or Firm—Reed F. Riley; William H. Magidson; Ralph C. Medhurst

[57] ABSTRACT

Described are magnesium compound-impregnated catalyst compositions comprising a gallium-modified, crystalline silica molecular sieve, essentially free of aliminum, composited in an inorganic matrix. Said compositions are useful fro hydrocarbon conversion, particularly the selective ethylation of toluene in which they exhibit extremely high paraselectivity at an excellent percent conversion.

2 Claims, No Drawings

SELECTIVE PARA-ETHYLATION OF TOLUENE WITH MAGNESIUM COMPOUND-IMPREGNATED, CRYSTALLINE, GALLOSILICATE BASED, MOLECULAR SIEVE CATALYST COMPOSITIONS

This is a continuation of application Ser. No. 901,613, filed Aug. 29, 1986, and now abandoned.

BACKGROUND OF THE INVENTION

This invention relates to the preparation of magnesium compound-impregnated catalyst compositions comprising a crystalline gallosilicate molecular sieve incorporated into an inorganic matrix and to processes for selectively ethylating toluene accomplished by contacting toluene and an ethylating agent under hydrocarbon conversion conditions with said compositions. More particularly, the invention relates to the preparation of magnesium compound-impregnated catalyst compositions comprising high surface area, essentially free of aluminum, crystalline gallosilicate-based molecular sieves incorporated into an inorganic matrix, and toluene conversion processes using such catalyst compositions comprising contacting ethylene and toluene under conversion conditions to form an ethyltoluene product in which the paraselectivity is nearly one hundred percent at excellent percent conversions.

In the commercial preparation of p-ethyltoluene for use to make p-methylstyrene, it is economically important that the method used to make the ethyltoluene makes a highly isomerically pure material. Separation of similar-in-property isomers prior to dehydrogenation of the ethyltoluene to the styrene compound is thus avoided. Paraselective catalysts useful for the gas-phase ethylation of toluene which can produce a product with greater than 95% isomeric purity are thus a highly desirable commercial objective.

A number of recent patents have claimed the formation of gallosilicate-type molecular sieves or gallium compound impregnated/exchanged sieves of various structures which are said to be useful for a variety of catalytic purposes. For example, U.S. Pat. Nos. 4,372,930 and 4,450,312 teach gallosilicate molecular sieves of Structure Types Nu-3 and Nu-5 which are claimed to be useful for the selective alkylation of alkanes and the isomerization of xylenes, respectively. U.S. Pat. No. 4,444,652 teaches the formation of gallium compound impregnated/exchanged sieves for upgrading low grade gasolines. In U.S. Pat. No. 4,377,502, the alkylation of toluene using a variety of crystalline aluminosilicate sieves is set forth. The patent teaches that the aluminum may be substituted by gallium. And in U.S. Pat. No. 4,276,437 ZSM-5 molecular sieve catalyst compositions impregnated with gallium and phosphorus compounds are taught for the selective paraethylation of toluene.

In Japanese Patent Application Kokai 60-19726 a gallosilicate of the ZSM-5 structure impregnated with a phosphorus oxide is used to improve alkylation paraselectivity when the sieve is used for the ethylation of toluene.

In U.S. Pat. Nos. 4,504,690, 4,128,592, and 4,086,287 the modifying of a ZSM-5 aluminosilicate zeolite catalyst with P, Mg, or P/Mg oxides to obtain high proportions of the 1,4-dialkyl isomer during alkylation is taught. Phosphorus or Mg-modified ZSM-5 zeolite catalysts for the disproportionation of toluene are described in J. Appl. Polym. Sci. 36, 209 (1981). Disproportionation of toluene to produce benzene over P, Mg-modified crystalline aluminosilicate zeolite catalysts is described in U.S. Pat. No. 4,137,195. Alkylation or disproportionation of certain monosubstituted benzene compounds to achieve nearly 100% selectivity to paradisubstituted derivatives over magnesium compound-modified ZSM-5 aluminosilicate zeolite catalysts is reported in J. Am. Chem. Soc. 101, 6783 (1979). Use of Mg alone or in combination with P to modify a ZSM-5 aluminosilicate zeolite catalyst is described in U.S. Pat. No. 4,049,573 and the modified catalyst is used for converting alcohols and ethers to hydrocarbons. Again, Mg is used to modify ZSM-5 zeolite catalysts in U.S. Pat. No. 4,002,698, which can be used for selective production of p-xylene from charge stocks of toluene and a $C_3$–$C_{10}$ olefin.

SUMMARY OF THE INVENTION

Described herein are magnesium compound-impregnated catalyst compositions comprising a high surface area, crystalline, gallosilicate molecular sieve, essentially aluminum free, incorporated into an inorganic matrix; said compositions when used to catalyze the ethylation of toluene are nearly one hundred percent paraselective at an excellent percent conversion. These magnesium compound-impregnated gallosilicate catalyst compositions are made in such a way that the gallium content of the sieve, while small, is incorporated differently in the crystalline lattice than gallium-containing sieves made by ion exchange or impregnation processes.

DETAILED DESCRIPTION OF THE INVENTION

The gallosilicate crystalline molecular sieves of this invention are characterized by the representative X-ray pattern listed in Table A below and by (0.2$_{2/n}$)the composition formula:

$$0.9 \pm 0.2 M_{2/n}O : Ga_2O_3 : ySiO_2 : zH_2O$$

wherein M is at least one cation, n is the valence of the cation, y is between 4 and about 600, and z is between 0 and about 160. It is believed that the small gallium content of the sieves is at least in part incorporated in the crystalline lattice. Various attempts to remove the gallium from the gallosilicate sieves by exhaustive exchange with sodium, ammonium, and hydrogen ions were unsuccessful and therefore, the gallium content is considered nonexchangeable in the instant sieves.

TABLE A

| d-Spacing Å (1) | Assigned Strength (2) | d-Spacing Å (1) | Assigned Strength (2) |
|---|---|---|---|
| 11.10 ± 0.20 | VS | 3.84 ± 0.10 | MS |
| 9.96 ± 0.20 | MS | 3.71 ± 0.10 | M |
| 6.34 ± 0.20 | W | 3.64 ± 0.10 | W |
| 5.97 ± 0.20 | W | 2.98 ± 0.10 | VW |
| 5.55 ± 0.20 | W | | |
| 4.25 ± 0.10 | VW | | |

(1) Copper K alpha radiation
(2) VW = very weak; W = weak; M = medium; MS = medium strong; VS = very strong The gallosilicate molecular sieve useful in this invention can be prepared by crystallizing an aqueous mixture, at a controlled pH, of a base, a gallium ion-affording material, an oxide of silicon, and an organic template compound.

Typically, the mol ratios of the various reactants can be varied to produce the crystalline gallosilicates of this invention. Specifically, the mol ratios of the initial reactant concentrations are indicated below:

|  | Broad | Preferred | Most Preferred |
|---|---|---|---|
| $SiO_2/Ga_2O_3$ | 4–200 | 10–150 | 20–100 |
| Organic base/$SiO_2$ | 0.5–5 | 0.05–1 | 0.1–0.5 |
| $H_2O/SiO_2$ | 5–80 | 10–50 | 20–40 |
| Temmplate/$SiO_2$ | 0–1 | 0.01–0.2 | 0.02–0.1 |

By regulation of the quantity of gallium (represented as $Ga_2O_3$) in the reaction mixture, it is possible to vary the $SiO_2/Ga_2O_3$ molar ratio in the final product. In general, it is desirable to have the gallium content of the gallosilicate sieve of this invention between about 0.1 and about 8 percent by weight of gallium. More preferably, the amount of gallium should be between about 0.2 and about 6 weight percent gallium and, most preferably, between about 0.3 and about 4 weight percent of gallium. Too much gallium in the reaction mixture appears to reduce the sieve crystallinity which reduces the catalytic usefulness of the sieve.

More specifically, the material useful in the present invention is prepared by mixing a base, a gallium ion-affording substance, an oxide of silicon, and an organic template compound in water (preferably distilled or deionized). The order of addition usually is not critical although a typical procedure is to dissolve the organic base and the gallium ion-affording substance in water and then add the template compound. Generally, the silicon oxide compound is added with mixing and the resulting slurry is transferred to a closed crystallization vessel for a suitable time. After crystallization, the resulting crystalline product can be filtered, washed with water, dried, and calcined.

During preparation, acidic conditions should be avoided. Advantageously, the pH of the reaction mixture falls within the range of about 9.0 to about 13.0; more preferably between about 10.0 and about 12.0 and most preferably between about 10.5 and 11.5.

Examples of oxides of silicon useful in this invention include silicic acid, sodium silicate, tetraalkyl silicates, and Ludox, a stabilized polymer of silicic acid manufactured by E. I. DuPont de Nemours & Co. Typically, the oxide of gallium source is a water-soluble gallium compound such as gallium nitrate or gallium acetate or another gallium compound, the anion of which is easily removed during sieve calcination prior to use. Water insoluble gallium compounds such as the oxide can be used as well.

Cations useful in formation of the gallosilicate sieves include the sodium ion and the ammonium ion. The sieves also can be prepared directly in the hydrogen form with an organic base such as ethylenediamine.

The acidity of the gallosilicate sieves of this invention is high as measured by the Hammett $H_o$ function which lies in the neighborhood of about $-3$ to about $-6$.

Organic templates useful in preparing the crystalline gallosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

The crystalline gallosilicate molecular sieve can be prepared by crystallizing a mixture of sources for an oxide of silicon, an oxide of gallium, an alkylammonium compound, and a base such as sodium hydroxide, ammonium hydroxide or ethylenediamine such that the initial reactant molar ratios of water to silica range from about 5 to about 80, preferably from about 10 to about 50 and most preferably from about 20 to about 40. In addition, preferable molar ratios for initial reactant silica to oxide of gallium range from about 4 to about 200, more preferably from about 10 to about 150 and most preferably from about 20 to about 100. The molar ratio of base to silicon oxide should be about above about 0.5, typically below about 5, preferably between about 0.05 and about 1.0 and most preferably between about 0.1 and about 0.5. The molar ratio of aklylammonium compound, such as tetra-n-propylammonium bromide, to silicon oxide can range from 0 to about 1 or above, typically above about 0.005, preferably about 0.01 to about 0.2, most preferably about 0.02 to about 0.1.

The resulting slurry is transferred to a closed crystallization vessel and reacted usually at a pressure at least the vapor pressure of water for a time sufficient to permit crystallization which usually is about 0.25 to about 25 days, typically is about one to about ten days and preferably is about one to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about three to about seven days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50° to about 225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, the mildly dried product is calcined at temperatures ranging from about 260° to about 850° C. and preferably from about 425° to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 hours. The gallosilicate sieves thus made generally have a surface area greater than about 300 sq. meters per gram as measured by the BET procedure.

The gallosilicate sieve useful in this invention is admixed with or incorporated within various binders or matrix materials depending upon the intended process use. The crystalline gallosilicates are combined with active or inactive materials, synthetic or naturally occurring zeolites, as well as inorganic or organic materials which would be useful for binding the gallosilicate. Well-known materials include silica, silica-alumina, alumina, magnesia, titania, zirconia, alumina sols, hydrated aluminas, clays such as bentonite or kaolin, or other binders well known in the art. Typically, the gallosilicate is incorporated within a matrix material by blending with a sol of the matrix material and gelling the resulting mixture or slurrying the sieve with the matrix material and drying. Also, solid particles of the gallosilicate and matrix material can be physically admixed. Typically, such gallosilicate compositions can be pelletized or extruded into useful shapes. The crystalline gallosilicate content can vary anywhere from a few up to 100 weight percent of the total composition. Catalytic compositions can contain about 0.1 weight percent to about 100 weight percent crystalline gallosilicate material and preferably contain about 10 weight percent to about 95 weight percent of such material and most preferably contain about 20 weight percent to about 80 weight percent of such material.

More specifically, catalytic compositions comprising the crystalline gallosilicate material and a suitable matrix material can be formed by adding a finely divided crystalline gallosilicate sieve to an aqueous sol or gel of the matrix material, such as PHF Alumina made by American Cyanamid Co. The resulting mixture is thoroughly blended and gelled, typically by adding a material such as ammonium hydroxide. The resulting gel is dried below about 200° C., more preferably between about 100° C. and about 150° C. and calcined between about 350° C. and about 700° C. to form a catalyst composition in which the crystalline gallosilicate sieve is distributed throughout the matrix material.

Alternatively, the sieve and a suitable matrix material like alpha-alumina monohydrate such as Conoco Catapal SB Alumina can be slurried with a small amount of a dilute weak acid such as acetic acid, dried at a suitable temperature under about 200° C., preferably about 100° to about 150° C. and then calcined at between about 350° and about 700° C., more preferably between about 400° to about 650° C.

Silica-supported catalyst compositions can be made by dry mixing the gallosilicate sieve with a silica source such as Cab-O-Sil, adding water and stirring. The resulting solid is then dried below about 200° C. and finally calcined between about 350° C. and 700° C.

To make an impregnated catalyst composition of this invention, a composition comprising the crystalline gallosilicate molecular sieve in an inorganic matrix is contacted with a magnesium compound-containing solution. The resulting mass is dried at temperatures up to about 150° C., driving off in this step essentially all of the impregnation solvent. The resulting composition is then activated by calcination for about 1 hour to about 24 hours at temperatures between about 300° C. and about 800° C., more preferably about 4 hours to about 24 hours at a temperature between about 400° C. to about 600° C.

The amount of magnesium incorporated within the catalyst composition should be from about 2 percent to 25 percent by weight, more preferably from about 4 percent to about 20 percent by weight, weight percents calculated as weight percent magnesium. The incorporated magnesium is believed to be present substantially in the oxide form.

Preferred magnesium compounds include most soluble magnesium salts, more preferably magnesium nitrate or acetate is used.

The solutions of magnesium compounds used in impregnation may be made from polar or nonpolar solvents, including water and organic solvents generally. Solvents that are destructive of either the zeolite or matrix should be avoided. Water and alcohol are preferred solvents.

Catalyst compositions of this invention are useful in hydrocarbon conversion reactions. A particularly useful reaction is alkylation of aromatics and especially the selective para-ethylation of toluene.

Ethylation of toluene in the presence of the above-described catalyst compositions is effected by contact of the toluene with ethlylene, preferably in the gas phase, at a temperature between about 200° and about 600° C. and preferably between about 250° and about 400° C. The reaction generally takes place at atmospheric pressure, but the pressure may be within the approximate range of about 1 atmosphere to about 2000 psig. The molar ratio of toluene to ethylene employed is within the approximate range of about 0.5 to about 50, more preferably about 2 to about 20. Reaction is suitably accomplished utilizing a weight hourly space velocity of between about 0.1 and about 100 and preferably between about 0.5 and about 50. The reaction product, consisting selectively of paraethyltoluene with comparatively smaller amounts of the other ethyl isomers, generally need not be separated for further use.

The following Examples will serve to illustrate certain specific embodiments of the hereindisclosed invention. These Examples should not, however, be construed as limiting the scope of the novel invention as there are many variations which may be made thereon without departing from the spirit of the disclosed invention, as those of skill in the art will recognize.

EXAMPLES

General

The hydrocarbon conversion test reactions of Example 17 below were carried out in a stainless steel reactor of plug-flow design. Reactants, in about an 8:1 toluene to ethylene mol ratio, were mixed and then fed into a pre-heater packed with inert Denstone packing and passed into a ½-inch O., D. ×5-inch reactor tube filled with a 3-5 g catalyst composition charge. The entire reactor and pre-heater assembly was supported in a fluidized sand bath maintained at reaction temperature. Product was collected in a cooled vessel as it dripped from the reactor and was analyzed by gas chromatography on a 60-meter fused silica capillary column. All hydrocarbon isomer amounts are given in percents by weight.

All catalyst compositions used contain 60 percent by weight support and 40 percent by weight sieve.

EXAMPLE 1

A 21.04 g portion of gallium nitrate was dissolved in water and to the solution was added 53.70 g of acetylacetone (AA) and 49.75 g of tetrapropylammonium bromide (TPA Br). After the AA and TPA Br had dissolved, a 353.02 g portion of Ludox AS-40 and a 31.95 g portion of sodium hydroxide were added. The resulting mixture which had a pH of 10.79 was transferred to a stainless steel autoclave and digested at 151° C. After 6 days digestion, the autoclave contents were filtered, and the solid material washed with water and dried at 151° C. for about 6 hours. The dried solid was calcined at 538° C. for 12 hours. The calcined solid was exchanged twice with a concentrated ammonium acetate solution and dried at 165° C. The sieve was analyzed and contained 2.48 weight percent gallium and 42.5 weight percent of silicon. It had a BET surface area of 380 sq m/g and a micropore volume of 0.1369 cc/g.

EXAMPLE 2

A 41.62 g portion of gallium nitrate was dissolved in water and to the solution was added 53.72 g of acetylacetone (AA) and 49.60 g of tetrapropylammonium bromide (TPA Br). After the AA and TPA Br had dissolved, a 352.76 g portion of Ludox AS-40 and a 41.50 g portion of sodium hydroxide were added. The resulting mixture which had a pH of 10.83 was transferred to a stainless steel autoclave and digested at 151° C. After 7 days digestion, the autoclave content was filtered, and the solid material washed with water and dried at 151° C. for about 6 hours. The dried solid was calcined at 538° C. for 12 hours. The calcined solid was exchanged twice with a concentrated ammonium acetate solution and dried at 165° C. The sieve was analyzed and found to contain 5.83 weight percent gallium and 39.8 weight percent silicon. It had a BET surface area of 295 sq m/g and a micropore volume of 0.0978 cc/g. A list of d-spacings and relative intensities from XRD follows below in Table B.

TABLE B

| d-Spacing Å (1) | Assigned Strength | d-Spacing Å (1) | Assigned Strength |
|---|---|---|---|
| 11.103 | VS | 4.595 | VW |
| 3.838 | MS | 2.480 | VW |
| 9.986 | M | 3.370 | VW |
| 3.711 | M | 2.727 | VW |
| 3.638 | W | 2.488 | VW |
| 5.968 | W | 1.663 | VW |
| 6.344 | W | 1.672 | VW |
| 5.554 | W | 3.994 | VW |
| 2.976 | VW | 2.401 | VW |
| 4.246 | VW | 1.447 | VW |
| 3.303 | VW | 1.667 | VW |
| 4.350 | VW | 2.391 | VW |
| 5.690 | VW | 1.394 | VW |
| 3.043 | VW | 2.604 | VW |
| 6.685 | VW | 1.914 | VW |
| 2.007 | VW | 2.413 | VW |
| 1.992 | VW | 1.871 | VW |
| 2.002 | VW | 1.457 | VW |
| 5.070 | VW | 2.856 | VW |
| 3.437 | VW | 1.459 | VW |
| 3.353 | VW | 1.865 | VW |
|  |  | 1.389 | VW |

(1) Copper K alpha radiation

EXAMPLE 3

A 1.59 g portion of gallium oxide slurried in water was added to 37.30 g of acetylacetone (AA) and 35.78 g of tetrapropylammonium bromide (PTA Br). After the AA and TPA Br had dissolved, a 252.30 g portion of Ludox AS-40 and a 15.2 g portion of sodium hydroxide were added. The resulting mixture which had a pH of 10.35 was transferred to a stainless steel autoclave and digested at 151° C. After 21 days digestion, the autoclave content was filtered, and the solid material washed with water and dried at 151° C. for about 6 hours. The dried solid was calcined at 538° C. for 12 hours. The calcined solid was exchanged twice with a concentrated ammonium acetate solution and dried at 165° C. The sieve was analyzed and found to contain 0.85 weight percent gallium and 43.08 weight percent silicon. It had a BET surface area of 337 sq m/g and a micropore volume of 0.0173 cc/g.

EXAMPLE 4

A 15 g portion of the sieve of Example 1 and 22.5 g Cab-O-Sil silica were dry mixed and transferred to a crystallizing dish with sufficient water to form a slurry. The mixture was heated at 150° C. until it gelled. The gel was dried at 130° C. for 16 hours and calcined at 600° C. On cooling, the catalyst composition was ground to 18/40 mesh.

EXAMPLE 5

A 10.5 g portion of $Mg(NO_3)_2.6H_2O$ dissolved in 50 ml of 50/50 water/ethanol was added to 5 g of the catalyst composition of Example 4. The mixture was stirred gently for 16 hours and the solvent removed using a rotary evaporator. The impregnated catalyst composition was dried at 130° C. for 16 hours and calcined at 600° C. The magnesium-impregnated catalyst composition contained 15.9 percent by weight magnesium.

EXAMPLE 6

The catalyst compositions of Example 4 was impregnated with a magnesium compound using the procedure of Example 5 except that a 3.94 g amount of the magnesium nitrate and 2.2 g of catalyst composition were used. The impregnated catalyst composition contained 14.3 percent magnesium.

EXAMPLE 7

A 10 g portion of the sieve of Example 1 was ground to a fine powder and dry mixed with 15 g of Conoco Catapal SB alumina. This mixture was stirred with 25 ml of 5 percent acetic acid and the resulting gel dried first at 130° C. for 16 hours and then calcined at 600° C. It was then ground to an 18/40-mesh powder.

EXAMPLE 8

A 5.01 g amount of $Mg(NO_3)_2.6H_2O$ in 30 ml of water was added to 4.75 g of the catalyst composition of Example 7. The result was stirred for 16 hours, dried first using a rotary evaporator and then at 130° C. for 16 hours. The dried, impregnated catalyst composition was then calcined at 600° C. The impregnated catalyst composition contained 7.0 percent magnesium.

EXAMPLE 9

A 10 g portion of the sieve of Example 2 was supported on 15 g of Conoco Catapal SB alumina by the method used in Example 7.

EXAMPLE 10

A 4 g portion of the catalyst composition of Example 9 was impregnated with 4.23 g of $Mg(NO_3)_2.6H_2O$ using the technique of Example 8. The impregnated catalyst composition contained 9.0 percent magnesium.

EXAMPLE 11

A 10 g portion of the sieve of Example 2 was supported on 15 g of Davison VFA alumina using the method of Example 7.

EXAMPLE 12

A 4 g portion of the sieve of Example 11 was treated with 30 ml of water containing 4.23 g of $Mg(NO_3)_2.6$-

H₂O. After stirring 6 hours, the water was removed with a rotary evaporator. The magnesium-impregnated catalyst composition was dried at 130° C. for 16 hours and calcined at 600° C. It contained 7.3 percent by weight magnesium.

COMPARATIVE EXAMPLE 13

A 44.5 g portion of the gallosilicate sieve of Example 3 was added to 66.44 g of Cab-O-Sil silica and blended. The mixture was transferred to a mixer and 110.06 g of water was added portionwise. Another 46.67 g of water was added giving a thixotropic mixture which was then treated with an additional 8.92 g of sieve and 13.45 g of Cab-O-Sil silica. The granular solid resulting was dried at 165° C. for 4 hours, calcined at 482° C. for 4 hours, and crushed and screened to an 18/40-mesh powder.

COMPARATIVE EXAMPLE 14

A mixture of 1200 ml of water, 107 ml of ethylenediamine, 96 g of tetra-n-propylammonium bromide and 40 g of Ludox HS-40 was briefly stirred and then loaded into a 21 Parr bomb autoclave. The closed bomb was heated at 165° C. with stirring for about 40 hours. After cooling, the contents were filtered, washed with 3000 ml of distilled water, dried 12 hours at 130° C, and calcined at 600° C. The material was found to contain about 184 ppm of aluminum.

COMPARATIVE EXAMPLE 15

A 10 g portion of the sieve of Comparative Example 14 was contacted with 15 ml of water containing 1.5 g of Ga(NO₃)₃.9H₂O for 6 hours. The water was evaporated and the resulting solid dried at 130° C. for 16 hours followed by calcination at 600° C. The resulting sieve contained 2.60 percent by weight gallium. A 10.3 g portion of the gallium-impregnated sieve was ground to a fine powder and dry mixed with 15.45 g of Cab-O-Sil silica. This mixture was slurried in water and heated at 150° C. with stirring until it gelled. The gallium-pregnated, silica-supported catalyst composition was dried at 130° C. for 16 hours and calcined at 600° C.

COMPARATIVE EXAMPLE 16

A 2.65 g portion of comparative Example 14 sieve was treated as in Comparative Example 15 with 0.56 g of Ga(NO₃)₃.9H₂O. The resulting sieve contained 3.42 percent by weight gallium. A 2 g portion of the resulting gallium-impregnated sieve was ground to a fine powder and dry mixed with 3 g of Catapal SB alumina. The mixture was treated with 8 ml of 5% acetic acid solution and the result stirred until it gelled. The gallium-impregnated, alumina-supported catalyst composition was dried at 130° C. for 16 hours and calcined at 600° C.

EXAMPLE 17

The catalyst compositions were tested for catalyst activity by the method under General above. The data is shown in Table C below.

TABLE C

| Catalyst Composition (Example No.) | T (°C.) | Conversion** (%) | Ethyltoluene Selectivity (%) | | |
|---|---|---|---|---|---|
| | | | Ortho | Meta | Para |
| 5 | 300 | 0.5 | * | 32.6 | 67.4 |
| 5 | 325 | 0.7 | * | ~2 | ~98 |
| 5 | 350 | 1.7 | * | ~2 | ~98 |
| 5 | 375 | 2.6 | * | ~2 | ~98 |
| 5 | 400 | 3.05 | * | 1.3 | ~98.7 |
| 6 | 300 | 1.2 | * | 6.7 | 93.3 |
| 6 | 325 | 2.7 | * | 2.6 | 97.4 |
| 6 | 350 | 4.6 | * | 2.9 | 97.1 |
| 6 | 400 | 7.3 | * | 4.3 | 95.7 |
| 8 | 300 | 1.7 | * | 18.7 | 81.3 |
| 8 | 325 | 2.7 | * | 3.4 | 96.6 |
| 8 | 350 | 4.8 | * | 5.7 | 94.3 |
| 8 | 375 | 6 | * | 8.4 | 91.6 |
| 10 | 300 | 0.6 | * | ~2 | ~98 |
| 10 | 325 | 2.2 | * | 1.1 | 98.9 |
| 10 | 350 | 4.6 | * | 1.3 | 98.7 |
| 10 | 375 | 5.7 | * | 1.8 | 98.2 |
| 12 | 300 | 1 | * | 4.1 | 95.9 |
| 12 | 325 | 1.2 | * | 3.8 | 96.2 |
| 12 | 350 | 1.8 | * | 2.3 | 97.7 |
| Comparative | | | | | |
| 13 | 325 | 2.6 | * | 6.1 | 93.9 |
| 13 | 350 | 3.7 | * | 6.6 | 93.4 |
| 13 | 375 | 4.6 | * | 8.0 | 92.0 |
| 13 | 300 | 1.7 | * | ~7 | ~93 |
| 15 | 300 | 0.2 | * | 10 | 90 |
| 15 | 300 | 0.2 | * | 24 | 76 |
| 15 | 300 | 0.3 | * | 23 | 77 |
| 16 | 325 | 0.2 | * | 29 | 71 |
| 16 | 325 | 0.35 | * | 22 | 78 |
| 16 | 325 | 0.5 | * | 20 | 80 |

*<0.01%
**Based on a toluene/ethylene feed ratio of 8:1. Maximum conversion is 12.5%

What is claimed is:

1. A gas-phase process to form para-ethyltoluene in greater than 95 weight percent isomeric purity comprising contacting toluene and ethylene at a temperature between about 250° C. to about 400° C. and in a mol ratio, toluene to ethylene, of about 2 to about 20 with a magnesium compound-impregnated catalyst composition containing between about 4 and about 20 weight percent magnesium comprising a crystalline silica molecular sieve, essentially aluminum-free and containing between about 0.3 and about 4 weight percent nonexchangeable gallium, composited in alumina or silica such that the composite contains between about 20 to about 80 percent by weight of said sieve, said sieve providing an X-ray pattern comprising the following X-ray diffraction lines and assigned strengths:

| Interplanar Spacing d, Å | Assigned Strength | Interplanar Spacing d, Å | Assigned Strength |
|---|---|---|---|
| 11.10 ± 0.20 | VS | 4.25 ± 0.10 | VW |
| 9.96 ± 0.20 | MS | 3.84 ± 0.10 | MS |
| 6.34 ± 0.20 | W | 3.71 ± 0.10 | M |
| 5.97 ± 0.20 | W | 3.64 ± 0.10 | W |
| 5.55 ± 0.20 | W | 2.98 ± 0.10 | VW |

2. A gas-phase process to form para-ethyltoluene in greater than 95 weight percent isomeric purity comprising contacting toluene and ethylene at a temperature between about 250° C. and about 400° C. and in a mol ratio, toluene to ethylene, of about 2 to about 20 with a magnesium compound-impregnated catalyst composition containing between about 4 and about 20 weight percent magnesium, said catalyst composition comprising a crystalline silica molecular sieve, essentially aluminum-free and containing between about 0.3 and about 4 weight percent nonexchangeable gallium, composited in alumina or silica such that the composite contains between about 20 to about 80 percent by weight of said sieve, said sieve made by crystallization from an aqueous solution containing a base, an organic templating material, a gallium ion-affording material and an oxide of silicon, and providing an X-ray pattern comprising the following X-ray diffraction lines and assigned strengths:

| Interplanar Spacing d, Å | Assigned Strength | Interplanar Spacing d, Å | Assigned Strength |
| --- | --- | --- | --- |
| 11.10 ± 0.20 | VS | 4.25 ± 0.10 | VW |
| 9.96 ± 0.20 | MS | 3.84 ± 0.10 | MS |
| 6.34 ± 0.20 | W | 3.71 ± 0.10 | M |
| 5.97 ± 0.20 | W | 3.64 ± 0.10 | W |
| 5.55 ± 0.20 | W | 2.98 ± 0.10 | VW |

* * * * *